(12) United States Patent
Kruse

(10) Patent No.: US 11,218,968 B2
(45) Date of Patent: *Jan. 4, 2022

(54) METHODS FOR REDUCTION OF BATTERY USAGE IN AMBULATORY INFUSION PUMPS

(71) Applicant: Tandem Diabetes Care, Inc., San Diego, CA (US)

(72) Inventor: Geoffrey A. Kruse, San Diego, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/676,118

(22) Filed: Nov. 6, 2019

(65) Prior Publication Data

US 2020/0077340 A1 Mar. 5, 2020

Related U.S. Application Data

(63) Continuation of application No. 15/354,495, filed on Nov. 17, 2016, now Pat. No. 10,492,141.

(60) Provisional application No. 62/256,398, filed on Nov. 17, 2015.

(51) Int. Cl.
*H04W 52/02* (2009.01)
*A61M 5/142* (2006.01)
*H04W 4/80* (2018.01)

(52) U.S. Cl.
CPC ........ *H04W 52/0232* (2013.01); *A61M 5/142* (2013.01); *H04W 4/80* (2018.02); *H04W 52/0251* (2013.01); *A61M 5/14244* (2013.01); *A61M 2205/18* (2013.01); *A61M 2205/3569* (2013.01); *A61M 2205/3584* (2013.01); *A61M 2205/50* (2013.01); *A61M 2205/52* (2013.01); *A61M 2205/8206* (2013.01); *A61M 2205/8212* (2013.01); *Y02D 30/70* (2020.08)

(58) Field of Classification Search
None
See application file for complete search history.

(56) References Cited

U.S. PATENT DOCUMENTS

| 2,898,088 A | 8/1959 | Alder |
| 2,936,788 A | 5/1960 | Dahl |
| 3,214,903 A | 11/1965 | Cochran |

(Continued)

FOREIGN PATENT DOCUMENTS

| CN | 1020175636 B | 12/2012 |
| EP | 1217275 B1 | 9/2004 |

(Continued)

OTHER PUBLICATIONS

Application and File history for U.S. Appl. No. 15/354,495, filed Nov. 16, 2016. Inventor: Kruse.

*Primary Examiner* — Ayaz R Sheikh
*Assistant Examiner* — Faiyazkhan Ghafoerkhan
(74) *Attorney, Agent, or Firm* — Patterson Thuente Pedersen, P.A.

(57) ABSTRACT

A battery-powered infusion pump for delivery of insulin or other medicament may collect and store data related to the pump. The infusion pump can communicate some or all of the stored data to another device, and control the timing and amount of data communicated in order to conserve battery life.

17 Claims, 5 Drawing Sheets

(56) References Cited

U.S. PATENT DOCUMENTS

| | | | |
|---|---|---|---|
| 3,430,659 A | 3/1969 | Henderson | |
| 5,135,499 A | 8/1992 | Tafani et al. | |
| 5,154,712 A | 10/1992 | Herweck et al. | |
| 5,207,666 A | 5/1993 | Idriss et al. | |
| 5,232,437 A | 8/1993 | Lysaght et al. | |
| 5,341,783 A | 8/1994 | Beck et al. | |
| 5,447,509 A | 9/1995 | Mills et al. | |
| 5,531,697 A | 7/1996 | Olsen et al. | |
| 5,531,698 A | 7/1996 | Olsen | |
| 5,562,079 A | 10/1996 | Gray, Jr. | |
| 5,628,324 A | 5/1997 | Sarbach | |
| 5,647,854 A | 7/1997 | Olsen et al. | |
| 5,676,651 A | 10/1997 | Larson, Jr. et al. | |
| 5,707,361 A | 1/1998 | Slettenmark | |
| 5,712,795 A * | 1/1998 | Layman | G01R 31/3648 700/297 |
| 5,759,018 A | 6/1998 | Thanscheidt | |
| 5,810,737 A | 9/1998 | Dardik | |
| 5,885,211 A | 3/1999 | Eppstein et al. | |
| 5,935,099 A | 8/1999 | Peterson et al. | |
| 5,954,752 A | 9/1999 | Mongeon et al. | |
| 6,012,492 A | 1/2000 | Kozyuk | |
| 6,016,044 A | 1/2000 | Holdaway | |
| 6,023,641 A | 2/2000 | Thompson | |
| 6,073,048 A | 6/2000 | Kieval et al. | |
| 6,123,686 A | 9/2000 | Olsen et al. | |
| 6,142,939 A | 11/2000 | Eppstein et al. | |
| 6,163,721 A | 12/2000 | Thompson | |
| 6,167,290 A | 12/2000 | Yang et al. | |
| 6,185,460 B1 | 2/2001 | Thompson | |
| 6,223,080 B1 | 4/2001 | Thompson | |
| 6,223,703 B1 | 5/2001 | Galvin | |
| 6,241,704 B1 | 6/2001 | Peterson et al. | |
| 6,309,371 B1 | 10/2001 | Deboer et al. | |
| 6,331,172 B1 | 12/2001 | Epstein et al. | |
| 6,413,254 B1 | 7/2002 | Hissong et al. | |
| 6,428,491 B1 | 8/2002 | Weiss | |
| 6,441,036 B1 | 8/2002 | Berge | |
| 6,450,942 B1 | 9/2002 | Lapanashvili et al. | |
| 6,475,180 B2 | 11/2002 | Peterson et al. | |
| 6,486,453 B1 | 11/2002 | Bales | |
| 6,512,949 B1 | 1/2003 | Combs et al. | |
| 6,520,936 B1 | 2/2003 | Mann | |
| 6,595,756 B2 | 7/2003 | Gray et al. | |
| 6,706,689 B2 | 3/2004 | Coolidge et al. | |
| 6,734,186 B1 | 5/2004 | Maw et al. | |
| 6,770,067 B2 | 8/2004 | Lorenzen et al. | |
| 6,851,449 B2 | 2/2005 | Kleibrink | |
| 6,894,024 B2 | 5/2005 | Coolidge et al. | |
| 6,899,699 B2 | 5/2005 | Enggaard | |
| RE38,749 E | 6/2005 | Dardik | |
| 6,932,584 B2 | 8/2005 | Gray et al. | |
| 6,945,760 B2 | 9/2005 | Gray et al. | |
| 6,970,742 B2 | 11/2005 | Mann et al. | |
| 6,981,499 B2 | 1/2006 | Anderson et al. | |
| 6,997,921 B2 | 2/2006 | Gray et al. | |
| 7,056,887 B2 | 6/2006 | Coolidge et al. | |
| 7,118,351 B2 | 10/2006 | Effenhauser et al. | |
| 7,131,967 B2 | 11/2006 | Gray et al. | |
| 7,136,701 B2 | 11/2006 | Greatbatch et al. | |
| 7,204,958 B2 | 4/2007 | Olsen et al. | |
| 7,220,365 B2 | 5/2007 | Qu et al. | |
| 7,320,675 B2 | 1/2008 | Pastore et al. | |
| 7,347,836 B2 | 3/2008 | Peterson et al. | |
| 7,371,418 B2 | 5/2008 | Sheabar et al. | |
| 7,396,353 B2 | 7/2008 | Lorenzen et al. | |
| 7,416,644 B2 | 8/2008 | Bonde | |
| 7,440,806 B1 | 10/2008 | Whitehurst et al. | |
| 7,483,743 B2 | 1/2009 | Mann et al. | |
| 7,493,171 B1 | 2/2009 | Whitehurst et al. | |
| 7,558,629 B2 | 7/2009 | Keimel et al. | |
| 7,572,789 B2 | 8/2009 | Cowen et al. | |
| 7,590,443 B2 | 9/2009 | Bharmi | |
| 7,650,181 B2 | 1/2010 | Freeman et al. | |
| 7,654,976 B2 | 2/2010 | Peterson et al. | |
| 7,654,982 B2 | 2/2010 | Carlisle et al. | |
| 7,678,833 B2 | 3/2010 | Ott | |
| 7,762,793 B2 | 7/2010 | Gray et al. | |
| 7,785,293 B2 | 8/2010 | Gray et al. | |
| 7,837,648 B2 | 11/2010 | Blair et al. | |
| 7,914,500 B2 | 3/2011 | Gafner-Geiser et al. | |
| 7,931,864 B2 | 4/2011 | Kloepfer et al. | |
| 8,016,783 B2 | 9/2011 | Pastore et al. | |
| 8,075,503 B2 | 12/2011 | Jaeb | |
| 8,094,009 B2 | 1/2012 | Allen et al. | |
| 8,099,074 B2 * | 1/2012 | Ebner | H04W 52/0216 455/343.3 |
| 8,105,265 B2 | 1/2012 | Demers et al. | |
| 8,130,095 B2 | 3/2012 | Allen et al. | |
| 8,155,712 B2 * | 4/2012 | Gilb | H04W 52/287 455/574 |
| 8,287,495 B2 | 10/2012 | Michaud et al. | |
| 8,287,514 B2 | 10/2012 | Miller et al. | |
| 8,323,188 B2 | 12/2012 | Tran | |
| 8,323,245 B2 | 12/2012 | List et al. | |
| 8,414,563 B2 | 4/2013 | Kamen et al. | |
| 8,472,913 B2 | 6/2013 | Ebner et al. | |
| 8,573,027 B2 | 11/2013 | Rosinko et al. | |
| 8,641,671 B2 | 2/2014 | Michaud et al. | |
| 8,852,152 B2 | 10/2014 | Tverskoy | |
| 8,903,350 B2 | 12/2014 | Ebner et al. | |
| 8,986,253 B2 | 3/2015 | DiPerna | |
| 9,101,714 B2 | 8/2015 | Miyazaki et al. | |
| 9,215,671 B2 * | 12/2015 | Zhao | H04W 52/288 |
| 9,381,297 B2 | 7/2016 | Brown et al. | |
| 9,555,186 B2 | 1/2017 | Kruse | |
| 9,750,873 B2 | 9/2017 | Brown et al. | |
| 10,492,141 B2 * | 11/2019 | Kruse | H04W 4/02 |
| 10,736,037 B2 | 8/2020 | Kruse et al. | |
| 2002/0018720 A1 | 2/2002 | Carlisle et al. | |
| 2003/0160683 A1 * | 8/2003 | Blomquist | A61M 5/142 340/309.16 |
| 2003/0225360 A1 | 12/2003 | Eppstein | |
| 2004/0015132 A1 | 1/2004 | Brown | |
| 2004/0167464 A1 * | 8/2004 | Ireland | G16H 20/17 604/66 |
| 2004/0172290 A1 * | 9/2004 | Leven | A61B 5/002 705/2 |
| 2006/0147313 A1 | 7/2006 | Zengerle et al. | |
| 2007/0173712 A1 | 7/2007 | Shah et al. | |
| 2007/0224951 A1 * | 9/2007 | Gilb | H04B 7/0691 455/127.5 |
| 2007/0293843 A1 * | 12/2007 | Ireland | G16H 40/67 604/504 |
| 2007/0299324 A1 * | 12/2007 | Rasch-Menges | A61B 5/0002 600/301 |
| 2008/0004601 A1 * | 1/2008 | Jennewine | G16H 40/63 604/890.1 |
| 2008/0065007 A1 * | 3/2008 | Peterson | F04B 51/00 604/65 |
| 2008/0065016 A1 | 3/2008 | Peterson et al. | |
| 2008/0177154 A1 | 7/2008 | Hansen et al. | |
| 2008/0177155 A1 | 7/2008 | Hansen et al. | |
| 2008/0222246 A1 | 9/2008 | Ebling et al. | |
| 2008/0269673 A1 * | 10/2008 | Butoi | A61M 5/14244 604/67 |
| 2008/0281297 A1 | 11/2008 | Pesach | |
| 2009/0006129 A1 * | 1/2009 | Thukral | G16H 20/10 705/2 |
| 2009/0062729 A1 * | 3/2009 | Woo | A61M 5/1723 604/66 |
| 2009/0069749 A1 | 3/2009 | Miller et al. | |
| 2009/0088821 A1 * | 4/2009 | Abrahamson | A61N 1/37252 607/60 |
| 2009/0118592 A1 * | 5/2009 | Klitgaard | A61B 5/6849 600/300 |
| 2009/0153148 A1 * | 6/2009 | Greenwald | A61M 5/365 324/639 |
| 2009/0177142 A1 | 7/2009 | Blomquist et al. | |
| 2010/0152811 A1 | 6/2010 | Flaherty | |
| 2010/0191074 A1 * | 7/2010 | Chou | G16H 40/67 600/301 |
| 2010/0198183 A1 | 8/2010 | Lanigan et al. | |

(56) References Cited

U.S. PATENT DOCUMENTS

| | | | |
|---|---|---|---|
| 2010/0250697 A1 | 9/2010 | Hansen et al. | |
| 2010/0274323 A1* | 10/2010 | Williamson | A61N 1/37276 607/60 |
| 2011/0110281 A1* | 5/2011 | Mehta | G16H 20/17 370/310 |
| 2011/0125095 A1* | 5/2011 | Lebel | G16H 20/17 604/151 |
| 2011/0144586 A1* | 6/2011 | Michaud | F16J 15/56 604/151 |
| 2011/0152824 A1 | 6/2011 | Diperna et al. | |
| 2011/0169610 A1* | 7/2011 | Geissler | H04Q 9/00 340/10.1 |
| 2011/0190694 A1* | 8/2011 | Lanier, Jr. | A61M 5/14224 604/67 |
| 2011/0266999 A1* | 11/2011 | Yodfat | A61M 5/14248 320/107 |
| 2011/0275904 A1* | 11/2011 | Lebel | G16H 20/17 600/300 |
| 2012/0022324 A1* | 1/2012 | Forsell | A61F 2/26 600/40 |
| 2012/0029941 A1* | 2/2012 | Malave | A61M 5/172 705/3 |
| 2012/0116197 A1* | 5/2012 | Moberg | A61M 5/14244 600/365 |
| 2012/0203178 A1 | 8/2012 | Tverskoy | |
| 2012/0216297 A1* | 8/2012 | Cohen | G16H 20/30 726/28 |
| 2013/0042194 A1* | 2/2013 | Gannon | G06Q 10/10 715/771 |
| 2013/0053816 A1* | 2/2013 | DiPerna | A61M 5/1408 604/500 |
| 2013/0088365 A1* | 4/2013 | Scordilis | H04B 17/00 340/870.02 |
| 2013/0123584 A1* | 5/2013 | Sun | A61N 1/36135 600/301 |
| 2013/0159456 A1* | 6/2013 | Daoud | G16H 20/17 709/217 |
| 2013/0196703 A1* | 8/2013 | Masoud | G16H 40/20 455/512 |
| 2013/0344813 A1* | 12/2013 | Ebner | A61M 5/1723 455/66.1 |
| 2013/0345658 A1* | 12/2013 | Browne | A61M 5/16831 604/500 |
| 2014/0054883 A1* | 2/2014 | Lanigan | A61M 39/1011 285/33 |
| 2014/0113553 A1* | 4/2014 | Brukalo | G16H 20/17 455/41.1 |
| 2014/0213977 A1* | 7/2014 | Miller | A61M 5/172 604/151 |
| 2014/0371816 A1* | 12/2014 | Matos | A61N 1/39622 607/59 |
| 2015/0066531 A1* | 3/2015 | Jacobson | G06Q 30/018 705/2 |
| 2015/0077038 A1* | 3/2015 | Chao | H02J 50/80 320/103 |
| 2015/0119805 A1* | 4/2015 | Blomquist | G16H 40/40 604/151 |
| 2015/0157793 A1* | 6/2015 | Kovelman | A61B 5/14532 600/365 |
| 2015/0273147 A1* | 10/2015 | Duke | A61M 5/1723 604/504 |
| 2016/0015888 A1* | 1/2016 | Tieck | G01V 3/02 137/551 |
| 2016/0080365 A1* | 3/2016 | Baker | H04L 63/083 726/4 |
| 2016/0287782 A1 | 10/2016 | Brown et al. | |
| 2017/0142658 A1* | 5/2017 | Kruse | H04W 52/0232 |
| 2018/0093039 A1* | 4/2018 | Estes | A61B 34/10 |
| 2018/0161498 A1* | 6/2018 | Estes | A61M 5/14244 |
| 2019/0307952 A1 | 10/2019 | Butler et al. | |
| 2020/0077340 A1* | 3/2020 | Kruse | H04W 52/0232 |
| 2020/0206420 A1 | 7/2020 | Michaud | |
| 2020/0329433 A1 | 10/2020 | Kruse et al. | |

FOREIGN PATENT DOCUMENTS

| | | | |
|---|---|---|---|
| WO | WO-2007065944 A1 * | 6/2007 | ........... A61B 5/6849 |
| WO | WO-2008103175 A1 | 8/2008 | |
| WO | WO-2009035753 A2 | 3/2009 | |
| WO | WO-2011014704 A2 | 2/2011 | |
| WO | WO-2011022850 A2 | 3/2011 | |
| WO | WO-2012034084 A2 | 3/2012 | |

* cited by examiner

METHODS FOR REDUCTION OF BATTERY USAGE IN AMBULATORY INFUSION PUMPS

RELATED APPLICATIONS

This application is a continuation of application Ser. No. 15/354,495 filed Nov. 17, 2016, which claims the benefit of U.S. Provisional Application No. 62/256,398 filed Nov. 17, 2015, each of which is hereby incorporated herein in its entirety by reference.

FIELD OF THE INVENTION

The present invention relates to infusion pumps and, more particularly, to reducing power usage in battery powered ambulatory infusion pumps.

BACKGROUND

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. patent application Ser. No. 13/838,617, U.S. patent application Ser. No. 13/827,707 and U.S. Pat. No. 8,287,495, each of which is incorporated herein by reference in its entirety.

Ambulatory infusion pumps as described above typically rely on one or more batteries to power the drive mechanism of the pump to deliver medicament. Many such ambulatory infusion pumps are programmable and include data storage and review features accessed through user interfaces of the devices. Many such pumps also enable wireless communications with other devices, such as continuous glucose monitors and data storage devices, through communications protocols such as Bluetooth or the like. Each of these and other features that can be a part of ambulatory infusion pumps further require power from the pump battery. However, in order for such pumps to be of a size to be conveniently carried by a user, there is limited space for the one or more batteries and therefore limited battery capacity. As such, there is a need in the art for ways in which to preserve battery power while still enabling full functional use of such ambulatory infusion pumps.

SUMMARY OF THE INVENTION

Systems and methods for conserving battery life of a medical device and/or a smartphone are provided herein. Mobile phones such as smartphones, may aid in determining, programming and data tracking therapy provided by a medical device such as an insulin pump. A smartphone can be in wireless communication with an insulin pump and can also be capable of connecting to one or more additional devices, such as a blood glucose meter, a therapy management system or a cloud storage service means. The smartphone can facilitate the transfer of data and measurements between and among these devices. Data may comprise one or more parameters related to the infusion pump such as operating status or warning status, therapy related events such as delivery of a bolus, and/or patient related parameters such as blood glucose.

Embodiments disclosed herein may conserve battery life of the medical device and/or smartphone by limiting exchanges of information, or data transfers, between the medical device and smartphone and/or between the smartphone and one or more additional devices such as a cloud storage means. For example such data transfers may be event-based, time-based, proximity-based.

In one embodiment, the present invention comprises an infusion pump including a battery, a data storage means, a wireless communication means configured to communicate data related to the infusion pump to another device, and a processor. The processor may be configured to collect and store the data in the data storage means, and control communication of the data to another device so as to reduce energy consumption of the battery based on information contained in the data storage means.

In one embodiment, the present invention comprises a method for reducing energy consumption of a battery of an infusion pump, the method comprising collecting data related to the infusion pump, storing the data in a data storage means in the infusion pump, wirelessly communicating the data to another device, and controlling communication of the data so as to reduce energy consumption of the battery based on information contained in the data storage means.

In one embodiment, the present invention comprises a user-wearable infusion pump including a battery, a memory, a transceiver configured to wirelessly communicate data related to the infusion pump to another device, a connector configured for interfacing with an external power source, and a processor. The processor may be configured to collect and store the data in the memory, and control communication of the data to another device so as to reduce energy consumption of the battery by communicating only part of the stored data while the infusion pump is powered by the battery, and by communicating additional stored data upon connection of the infusion pump to an external power source via the connector.

Certain embodiments are described further in the following description, examples, claims, and drawings. These embodiments will become more apparent from the following detailed description when taken in conjunction with the accompanying exemplary drawings.

BRIEF DESCRIPTION OF THE DRAWINGS

Subject matter hereof may be more completely understood in consideration of the following detailed description of various embodiments in connection with the accompanying figures, in which.

Figure 1:
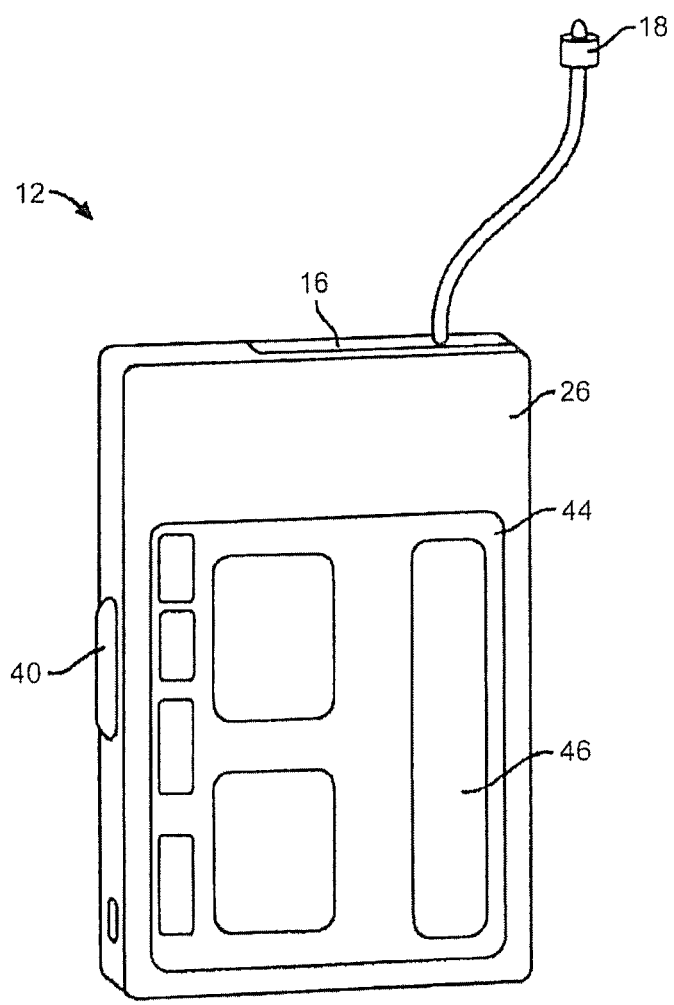
FIG. 1 is a medical device that can be utilized with embodiments of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an embodiment of a medical device that can be used with embodiments of the present invention. In this embodiment, the medical device is configured as a pump 12, such as an infusion pump, that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, graphene-based displays, OLED displays and the like. The output/display 44 may include an interactive and/or touch sensitive screen 46 having an input device such as, for example, a touch screen comprising a capacitive screen or a resistive screen. The pump 12 may additionally include a keyboard or other input device known in the art for data entry, which may be separate from the display. The pump 12 may additionally include one or more of a keyboard, microphone, or other input device known in the art for data entry, which such input device or devices may be separate from the display. The pump 12 may also include a capability to operatively couple to a secondary display device such as a remote display, a remote control device, a laptop computer, personal computer, tablet computer, mobile communication device such as a smartphone or personal digital assistant (PDA) or the like.

In one embodiment, the medical device can be a portable insulin pump configured to deliver insulin to a user or patient. Further details regarding such pump devices can be found in U.S. Patent Application No. 2011/0144586, which is incorporated herein by reference. In other embodiments, the medical device can be an infusion pump configured to deliver one or more additional or other medicaments to a patient. In a further embodiment, the medical device can include a glucose meter such as continuous glucose monitor. In other embodiments, the medical device can additionally or separately monitor one or more other physiological parameters of a patient.

Figure 2:
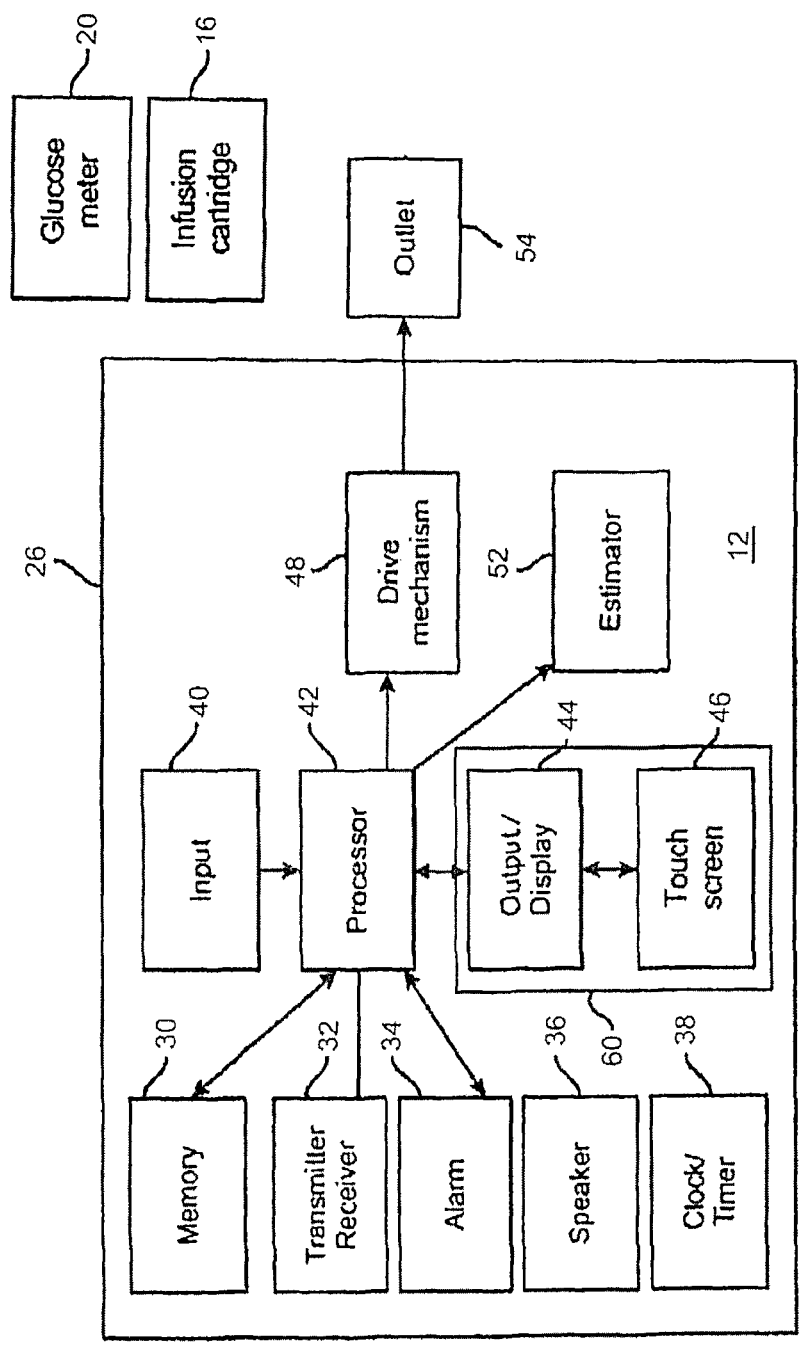
FIG. 2 is a block diagram representing a medical device that can be used with embodiments of the present invention.

FIG. 2 illustrates a block diagram of some of the features that can be used with embodiments of the present invention, including features that may be incorporated within the housing 26 of a medical such as the pump 12. The pump 12 includes a processor 42 that functions to control the overall functions of the device. The infusion pump 12 may also include, e.g., a data storage means such as a memory device 30, a communications means such as a transmitter/receiver (transceiver) 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, a transmitter/receiver and other components. In some embodiments, the processor 42 may communicate with another processor within the pump 12 and/or one or more processors of other devices, for example, a continuous glucose monitor (CGM), display device, smartphone, etc. through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature or other parameters.

The processor 42 may also include additional programming to allow the processor 42 to learn user preferences and/or user characteristics and/or user history data. This information can be utilized to implement changes in use, suggestions based on detected trends, such as, weight gain or loss. The processor can also include programming that allows the device to generate reports, such as reports based upon user history, compliance, trending, and/or other such data. Additionally, infusion pump device embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pumps, including a high power controller and a low power controller used to maintain programming and pumping functions in low power mode, in order to save battery life. In another embodiment, a first processor may be utilized for pump functions and a second processor may be utilized for communication functions.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more templates or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual square wave, basal and bolus rate profiles, and/or the like. The memory can also store, for example, user information, history of use, glucose measurements, compliance and an accessible calendar of events. The memory can also store limits on insulin doses that can be delivered based on CGM data, as discussed herein. The housing 26 of the pump 12 may be functionally associated with an interchangeable and removable glucose meter 20 and/or one or more infusion cartridges 16. The infusion cartridge 16 may have an outlet port 54 that may be connected to an infusion set (not shown) via an infusion set connector 18. Further details regarding some embodiments of various infusion pumps can be found in U.S. Patent Application No. 2011/0144586, which is hereby incorporated by reference in its entirety.

Figure 2A:
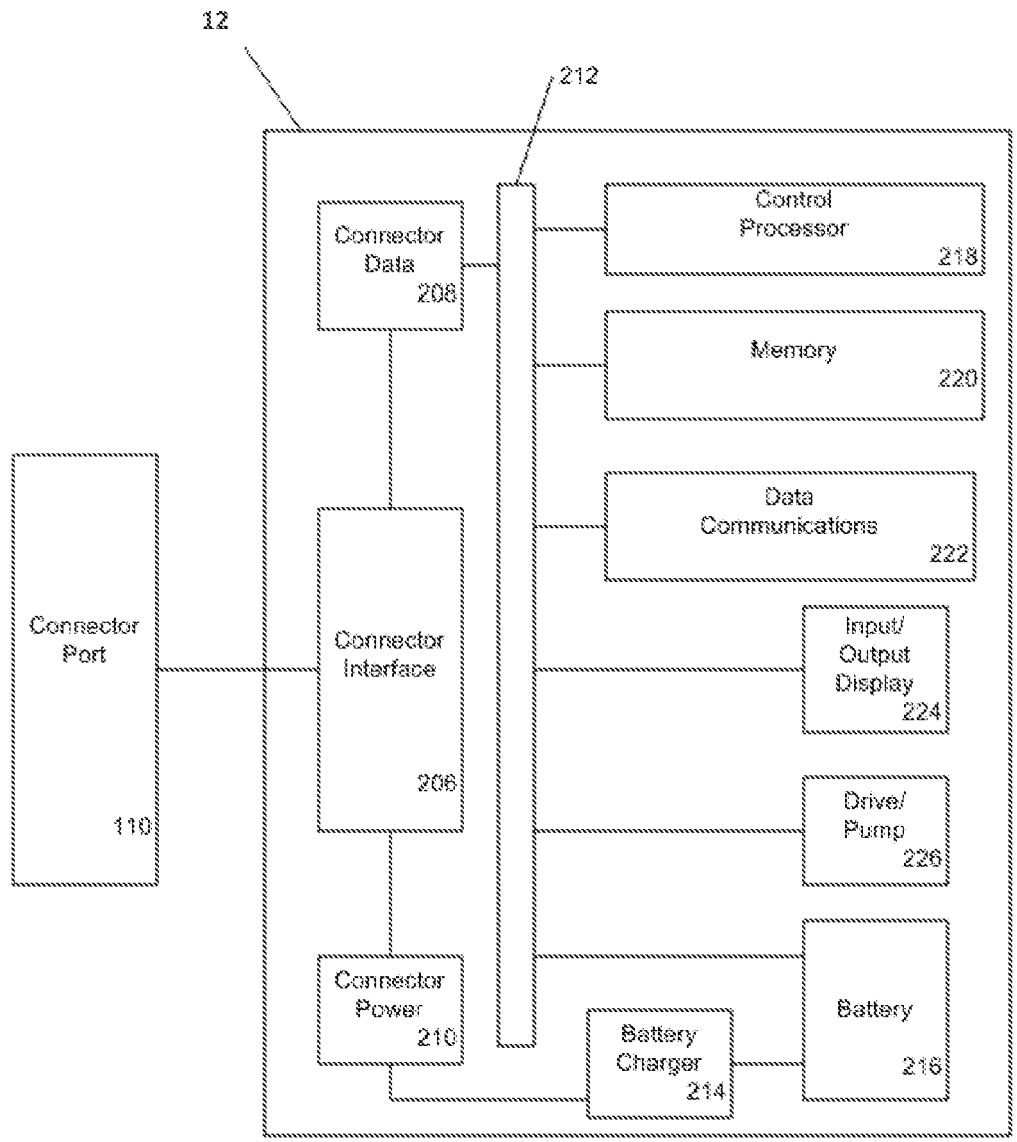
FIG. 2A is another block diagram representing a medical device that can be used with embodiments of the present invention.

FIG. 2A is another block diagram of some of the features that can be used with embodiments of the present invention. Pump 12 includes a power management system that is connected to the connector port 110 that receives a combined data/power cable, such as a USB cable. That is, the cable has the capability of simultaneously providing electrical energy for charging and data transmission for communications. A connector interface 206 supports data exchange and receives electrical power through the connector port 110, and controls a connector data element 208 and a connector power element 210. The device may be powered by battery power in place of or in addition to the connector interface. The connector interface 206 passes data communications from the connector port 110 through the connector data element 208 to a system bus 212. The connector interface 206 passes electrical power from the connector port 110 through the connector power element 210 to a battery charger 214, which in turn is coupled to a battery 216 and which recharges the battery. In one embodiment, the connector data element 208 is implemented in the FIG. 2A device with a USB Isolation Chip ADUM4160 product from Analog Devices, Inc. of Norwood, Mass., USA, and the connector power element 210 is implemented in the FIG. 2A device with a USB Power Isolation Chip LT3573 product from Linear Technology Corporation of Milpitas, Calif., USA. Those skilled in the art will be aware of alternative suitable devices.

A control processor 218 is connected to the system bus 212 and receives the data communications from the connector data element 208 for processing. The control processor controls operation of the various elements of the pump 12 that are connected to the system bus. The control processor operates according to program instructions that may be stored in device memory 220. Program instructions may be stored in processor memory incorporated in the control processor 218. The control processor also stores data from its operations in the device memory 220. The control processor 218 controls a data communications element 222 that may comprise a receiver/transmitter for wireless RF communications, such as "WiFi" communications or "Bluetooth" communications between the portable device 100 and compatible external systems and networks. The pump 12 includes an output/display element 224 such as a touchscreen display, operating buttons or switches, and the like. The pump 12 includes a drive/pump element 226 such as a pumping mechanism for delivery of fluid such as insulin via outlet port 54. To meet industry standards and governmental regulations, the connector data element 208 and the connector power element 210 are both electrically isolated from the other device components, so as to provide a device that can be safely connected to the power source and the patient at the same time.

Figure 3:
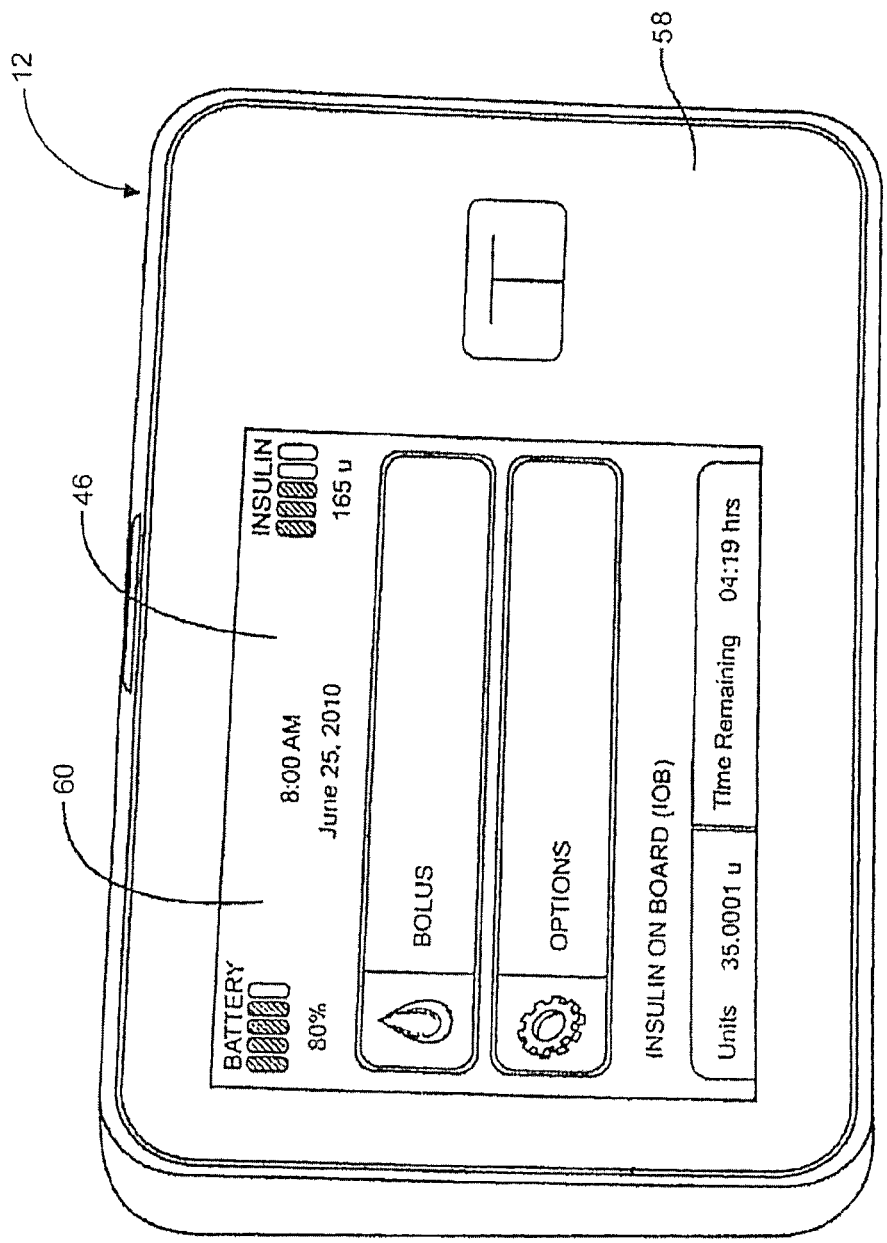
FIG. 3 depicts an exemplary screen shot of a home screen page of a user interface of a medical device such as an infusion pump that can be used with embodiments of the present invention.

The memory 220 of pump 12 may be any type of memory capable of storing data and retrieving that data for transfer to one or more other components of the device, such as the control processor 218. Memory 220 may comprise one or more of a Flash memory, SRAM, ROM, DRAM, RAM, EPROM or dynamic storage. Memory 220 may be coupled to the control processor 218 and may be configured to receive and store input data and/or store one or more template or predetermined fluid delivery patterns. For example, the memory can be configured to store one or more personalized (e.g., user defined) delivery profiles, such as a profile based on a user's selection and/or grouping of various input factors; past generated delivery profiles; recommended delivery profiles; one or more traditional delivery profiles, e.g., square wave, dual square wave, basal and bolus rate profiles; and/or the like. The memory can also store user information, history of use, glucose measurements, compliance, an accessible calendar of events, and the like. In some embodiments, the memory 220 of pump 12 may have a data capacity of up to about 10 GB, more specifically, up to about 3 GB, even more specifically, about 1 MB to about 200 MB. In some embodiments, the memory of pump 12 may be up to about 3 GB, more specifically, up to about 500 MB, and even more specifically, about 200 kB to about 200 MB. The embodiments depicted in FIG. 2 and FIG. 2A are not to be considered mutually exclusive, rather, components depicted in either may be interchanged between embodiments. Referring to FIG. 3, a front view of pump 12 is depicted. The pump 12 may include a user interface, such as, for example, a user-friendly GUI 60 on a front surface 58 or other location of pump 12. The GUI 60 may include a touch-sensitive screen 46 that may be configured for displaying data, facilitating data and/or command entry, providing visual tutorials, as well as other interface features that may be useful to the patient operating the pump 12. The GUI can also present alarm or alerts to the user.

Figure 4:
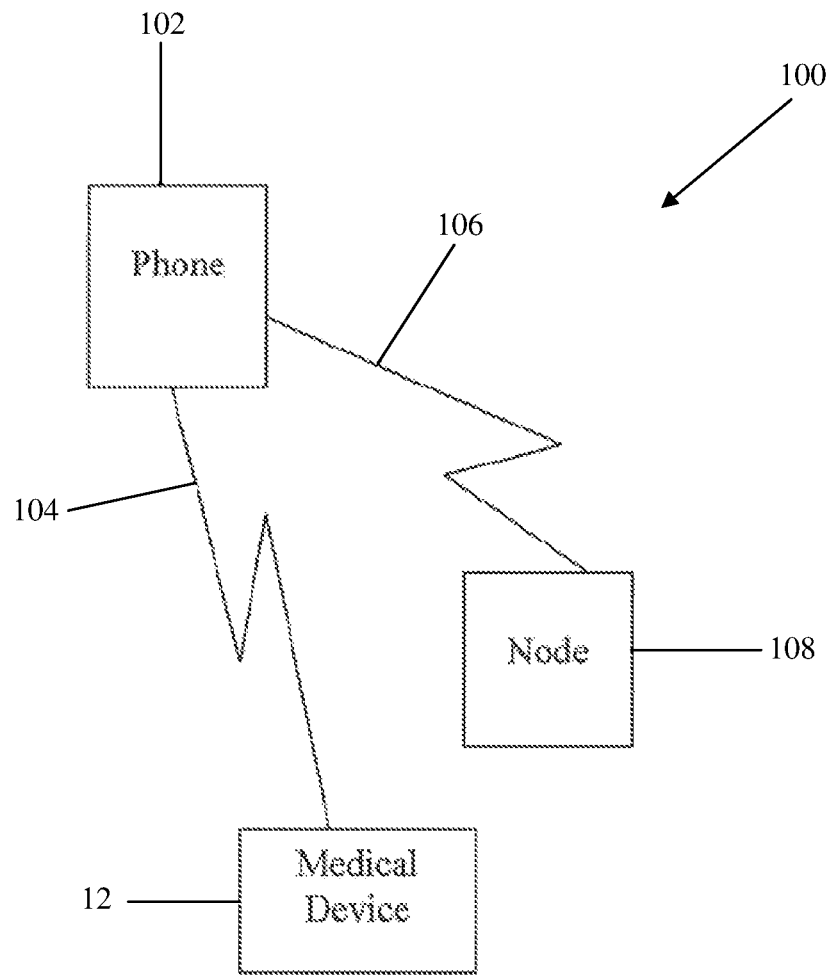
FIG. 4 is a schematic representation of a system according to embodiments of the present invention.

Referring now to FIG. 4, a system 100 according to embodiments of the present invention includes a medical device such as an insulin pump 12 having a wireless connection 104 to a mobile phone 102, such as a smartphone, via, for example, Bluetooth, Bluetooth low energy, mobile or Wi-Fi communications. Wireless connection 104 is established via transmitter/receiver 32. In some embodiments, the phone 102 can also have a wireless or wired connection 106 to one or more other nodes 108, such as a cloud storage service means, a blood glucose meter 108 or a continuous glucose monitor (CGM). Although the system 100 is described with respect to a mobile phone, alternate types of devices could be used in place of a phone as the device 102, including, for example, an electronic tablet or a laptop or desktop computer. Similarly, although described with respect to an insulin pump, the medical device 12 can be any other type of programmable medical device capable of wirelessly communication with a mobile phone 102 or other device, including, for example, infusion pumps for infusing medicaments other than insulin.

In embodiments wherein node 108 comprises a cloud storage service means for receiving data from phone 102 regarding pump 12, it is especially desired to conserve battery life of both pump 12 and phone 102. Phone 102 may comprise a master device, and pump 12 may comprise a slave device, such that phone 102 initiates and controls the transmission of data between phone 102 and pump 12, via, for example, Bluetooth or other wireless means. Phone 102 may include a program or application configured to receive and/or transmit data, instructions and/or other information between pump 12 and phone 102. Although pump 12 and phone 102 may be in constant or near-constant communication in an attempt to provide real-time feedback, such an arrangement may negatively impact battery life of both pump 12 and phone 102. Therefore, various embodiments herein provide improved methods of communication between pump 12 and phone 102 to prolong battery life of both devices.

Pump 12 may, for example, be configured to transmit Bluetooth advertising packets via transmitter/receiver 32, each packet containing a number of bits of information. Phone 102, via the Bluetooth connection 104, is configured to detect and receive the advertising packets transmitted by pump 12.

In some embodiments, the frequency of communications between pump 12 and phone 102 to transmit data may be modified to conserve battery power of one or both devices. In one embodiment, the frequency of communications may be event-based. For example, the event may comprise delivery of a bolus, change in basal delivery rate, triggering of an alarm or other predetermined event. Upon occurrence of such a predetermined event, processor 42 of pump 12 is configured to modify the contents of its next Bluetooth advertising packet to include an indication based on the event that phone 102 should initiate communication with pump 12 to transmit data regarding the event. This allows pump 12 to remain in a lower power, advertising state until phone 102 initiates communication resulting in pump 12 and phone 102 being paired. In one embodiment, a list of predetermined events is stored in memory device 30 of pump 12. In another embodiment, processor 42 includes programming having a list of predetermined events.

In another embodiment, each Bluetooth advertising packet from pump 12 may be configured to include an indication of pump status. Upon occurrence of a predetermined notable event requiring a data transfer between pump 12 and phone 102, the indication of pump status included in the Bluetooth advertising packet from pump 12 signals phone 102 to initiate communication with pump 12 to transmit data regarding the event.

In another embodiment, the frequency of wireless communications may be event-based but the amount of data transmitted varies according to the nature of the event. For example, for any events predetermined to be of a less important nature, pump 12 may transmit an indication to phone 102 that a data transfer is required at a later time when pump 12 is connected to an external power source via connector port 110 for recharging. For any events predetermined to be of a more important nature, pump 12 may transmit an indication that a data transfer is required immediately to transmit data regarding the event. The relationship between the nature of an event and the amount of data to be transmitted may be stored in memory device 30 or included as part of programming operable by processor 42.

In another embodiment, the frequency of wireless communications may be periodic, or time-based. For example, pump 12 may transmit an indication to phone 102 at predetermined intervals that a data transfer is required. Such intervals may comprise every 15 minutes, every 30 minutes, every 60 minutes, or any other desired interval. Contained in the periodic indication will be information regarding the pump, including for example basal rate, delivery of last bolus, any events that have occurred since the last data transmission, or other information stored by the pump. The frequency of wireless communications may be stored in memory device 30 or included as part of programming operable by processor 42.

In another embodiment, wireless communications between pump 12 and phone 102 may comprise only a partial subset of all available information. Pump 12 may transmit an indication to phone 102 that a data transfer is required, and upon initiation of the data transfer only transmit a partial subset of all available information stored by the pump. When pump 12 is connected to an external power source via connector port 110 for recharging, pump 12 transmits an indication to phone 102 to transfer all available saved data regarding pump 12. The data selected to be contained in the partial subset may be based on information stored in memory device 30 or included as part of programming operable by processor 42.

In another embodiment, wireless communications between pump 12 and phone 102 may be proximity-based. For example, phone 102 may rely on GPS information to initiate data transfer from pump 12 such that if a patient having phone 102 arrives at a specific location such as a hospital, clinic or other care facility, phone 102 may determine through GPS information that a complete data transfer is required from pump 12 in order to have the most current data available on phone 102 when the patient visits their care provider. A list of locations for full data transfers, and/or relationships between locations and the amount of data to be transferred, may be stored in memory device 30 or included as part of programming operable by processor 42.

In another embodiment, it is also desired to prolong battery life of phone 102. For example, when transferring information from phone 102 to node 108 such as a cloud storage service means for receiving data from phone 102 regarding pump 12. In one embodiment, transfers from phone 102 to node 108 are delayed until the cellular connection of phone 102 meets a predetermined minimum signal strength, or until phone 102 is connected to a wi-fi network, at which time data saved on phone 102 is transmitted to node 108.

In another embodiment, data transfers from phone 102 to node 108 only occur when the user of phone 102 first launches the application which controls data transfers, and/ or only when the user is actively using the application. In another embodiment, data transfers from phone 102 to node 108 only occur when phone 102 is connected to a power source and is being recharged.

In another embodiment, data transfers from phone 102 to node 108 are event-based, such data transfers are delayed until a predetermined event has occurred. Alternatively, data transfers may be delayed until a predetermined number of events have occurred. Alternatively, data transfers may be event-based but the amount of data transferred varies according to the nature of the event. For example, for events predetermined to be of a less important nature, the data transfer from phone 102 to node 108 may be delayed. Whereas events predetermined to be of a more important nature cause phone 102 to transfer data to node 108 upon occurrence of the event.

In another embodiment, data transfers from phone 102 to node 108 may be periodic, or time-based. For example, data transfers may occur at predetermined intervals such as every 15 minutes, every 30 minutes, every 60 minutes, or any other desired interval.

In another embodiment, data transfers from phone 102 to node 108 may be proximity-based. For example, phone 102 may rely on GPS information to initiate the data transfer such that if a patient having phone 102 enters a hospital, clinic or other care facility, phone 102 may determine through GPS information that a complete data transfer is required to node 108 in order to have the most current data available on phone 102 when the patient visits their care provider. The above described embodiments regarding conserving battery life of both pump 12 and phone 102 may be combined if desired. For example, the frequency of communications between pump 12 and phone 102 to transmit data may be event-based and time-based. Or, for example, one or more embodiments for conserving battery life of pump 12 may be combined with one or more embodiments for conserving battery life of phone 102. Other such combinations of energy-saving methods described herein are within the spirit and scope of the invention.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421; 8,448,824; 8,573,027; 8,650,937; 8,986,523; 9,173,998; 9,180,242; 9,180,243; 9,238,100; 9,242,043; and 9,335,910 commonly owned U.S. Patent Publication Nos. 2009/0287180; 2012/0123230; 2013/0053816; 2013/0159456; 2013/0324928; 2013/0331790; 2013/0332874; 2014/0273042; 2014/0276419; 2014/0276420; 2014/0276423; 2014/0276531; 2014/0276537; 2014/0276553; 2014/0276556; 2014/0276569; 2014/0276570; 2014/0276574; 2014/0378898; 2015/0073337; 2015/0072613; 2015/0182693; 2015/0182694; 2015/0182695; 2016/0030669; and 2016/0082188 and commonly owned U.S. patent application Ser. Nos. 14/707,851 and 15/158,125 and commonly owned U.S. Provisional Application Ser. Nos. 61/911,576; 61/920,902; 61/920,914; 61/920,940; 62/139,275; 62/207,748; 62/256,398; 62/272,255; 62/300,410; and 62/352,164.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An infusion pump, comprising:
a battery;
a memory;
a wireless communication interface configured to communicate data related to therapy provided by the infusion pump to another device; and
a processor configured to:
collect and store the data related to therapy provided by the infusion pump in the memory; and
control communication of the stored data related to therapy provided by the infusion pump to another device so as to reduce energy consumption of the battery, wherein controlling communication of the stored data so as to reduce energy consumption of the battery includes selectively delaying transmission of at least some of the stored data until a predetermined condition relating to treatment with the infusion pump is met.

2. The infusion pump of claim 1, wherein the predetermined condition is occurrence of a predetermined infusion pump therapy event.

3. The infusion pump of claim 1, wherein the processor is configured to communicate an indication of a status of the infusion pump to the another device.

4. The infusion pump of claim 1, wherein the processor is configured to transmit part of the stored data to the another device prior to the predetermined condition being met.

5. The infusion pump of claim 4, wherein the processor is configured to transmit additional stored data upon the predetermined condition being met.

6. The infusion pump of claim 1, wherein the predetermined condition is connection of the infusion pump to a power source.

7. The infusion pump of claim 1, wherein the predetermined condition is based on a geographic location of the infusion pump.

8. The infusion pump of claim 1, wherein the communication is via Bluetooth connection.

9. The infusion pump of claim 1, further comprising a connector configured for interfacing with an external power source.

10. A method of reducing energy consumption of a battery of an infusion pump, the method comprising: collecting data related to the infusion pump; storing the data in a memory in the infusion pump; wirelessly communicating the stored data to another device; and controlling communication of the data so as to reduce energy consumption of the battery based on information contained in the memory, wherein controlling communication of the stored data so as to reduce energy consumption of the battery includes selectively delaying transmission of at least some of the stored data until a predetermined condition relating to treatment with the infusion pump is met.

11. The method of claim 10, wherein the predetermined condition is occurrence of a predetermined infusion pump therapy event.

12. The method of claim 10, further comprising communicating an indication of a status of the infusion pump.

13. The method of claim 10, wherein controlling communication of the data comprises transmitting less than all of the stored data to the another device prior to the predetermined condition being met.

14. The method of claim 13, further comprising transmitting additional data to the another device upon the predetermined condition being met.

15. The method of claim 10, wherein the predetermined condition is connection of the infusion pump to a power source.

16. The method of claim 10, wherein the predetermined condition is based on a geographical location of the infusion pump.

17. The method of claim 10, wherein communication of the data is via Bluetooth connection.

* * * * *